United States Patent
Sekine et al.

(10) Patent No.: US 9,476,693 B2
(45) Date of Patent: Oct. 25, 2016

(54) OPTICAL PROPERTY MEASUREMENT APPARATUS AND OPTICAL PROPERTY MEASUREMENT METHOD

(71) Applicants: KABUSHIKI KAISHA TOPCON, Itabashi-ku (JP); THE UNIVERSITY OF ELECTRO-COMMUNICATIONS, Chofu-shi (JP)

(72) Inventors: Akihiko Sekine, Inagi (JP); Eriko Watanabe, Chofu (JP)

(73) Assignees: KABUSHIKI KAISHA TOPCON, Itabashi-ku (JP); The University of Electro-Communications, Chofu-shi (JP)

( * ) Notice: Subject to any disclaimer, the term of this patent is extended or adjusted under 35 U.S.C. 154(b) by 0 days.

(21) Appl. No.: 14/651,948

(22) PCT Filed: Dec. 4, 2013

(86) PCT No.: PCT/JP2013/082644
§ 371 (c)(1),
(2) Date: Jun. 12, 2015

(87) PCT Pub. No.: WO2014/091993
PCT Pub. Date: Jun. 19, 2014

(65) Prior Publication Data
US 2015/0323304 A1    Nov. 12, 2015

(30) Foreign Application Priority Data
Dec. 13, 2012 (JP) .................................. 2012-272290

(51) Int. Cl.
G01N 21/45  (2006.01)
G01B 9/02   (2006.01)
G01N 21/47  (2006.01)

(52) U.S. Cl.
CPC ....... *G01B 9/02091* (2013.01); *G01B 9/02004* (2013.01); *G01N 21/45* (2013.01); *G01N 21/4795* (2013.01)

(58) Field of Classification Search
CPC .......... G01B 9/02027; G01B 9/02091; G01N 21/00; G01N 21/45; G01N 2021/1734; G01N 2021/1736
USPC ................................................. 356/481, 517
See application file for complete search history.

(56) References Cited

U.S. PATENT DOCUMENTS

| 7,978,336 B2 * | 7/2011 | Mann ..................... G01B 9/021 356/485 |
| 2003/0053072 A1 | 3/2003 | Fercher et al. |
| 2010/0007894 A1 | 1/2010 | Suehira |
| 2013/0222785 A1 * | 8/2013 | Sasaki ..................... G01C 3/08 356/4.09 |

FOREIGN PATENT DOCUMENTS

| JP | 2001-212086 A | 8/2001 |
| JP | 2003-543 A | 1/2003 |
| JP | 2007-101365 A | 4/2007 |
| JP | 2008-304456 A | 12/2008 |
| JP | 2009-264787 A | 11/2009 |
| JP | 2010-19636 A | 1/2010 |

OTHER PUBLICATIONS

International Search Report issued Mar. 11, 2014, in PCT/JP2013/082644, filed Dec. 4, 2013.

\* cited by examiner

*Primary Examiner* — Jonathan Hansen
(74) *Attorney, Agent, or Firm* — Oblon, McClelland, Maier & Neustadt, L.L.P (57) ABSTRACT

An apparatus enabling abnormality detection of a sample. A first interference optical system scans the sample with first signal light from a first sample optical path, making the first signal light interfere with first reference light from a first reference optical path, to detect first interference light. Optical path length difference between the first sample optical path and first reference optical path is changed based on the detection. A change in the optical path length difference is determined. A second interference optical system scans the sample with second signal light from a second sample optical path, making the second signal light interfere with second reference light from a second reference optical path to detect second interference light. Tomographic information of the sample based on detection of the second interference light is determined. A refractive index profile of the sample is obtained based on the change amount information and tomographic information.

14 Claims, 7 Drawing Sheets

OPTICAL PROPERTY MEASUREMENT APPARATUS AND OPTICAL PROPERTY MEASUREMENT METHOD

TECHNICAL FIELD

Embodiments described herein relate generally to an optical property measurement apparatus and an optical property measurement method.

BACKGROUND TECHNOLOGY

In recent years, treatments using cell sheets are becoming more widespread. In particular, treatments of transplanting cell sheets made of the patient's own cells have been being established. In such treatments, stem cells are extracted from cells taken from a patient, and myocardial or corneal epithelial/endothelial cells are cultured to create a cell sheet.

The cell sheet needs to be created in a state suitable for transplantation. For example, it is required for the cell sheet for the cornea that cells are properly stratified without a loss and the like. The inspection for this is performed after the culture. Since the cornea is transparent, it cannot be observed with an ordinary microscope. Therefore, phase contrast imaging is performed by a phase-contrast microscope to detect the presence or absence of an abnormality in the cell sheet.

Although inspection using a phase-contrast microscope is simple and the existence of the optical path length differences and the distribution thereof can be observed as irregularities of the pattern due to the phase contrast, it cannot be figured out the degrees of the differences actually exists.

Besides, in the fields of high-density optical memory and optical communication/information processing, for the purpose of understanding the refractive index modulation amount and the refractive index difference, there has been a growing interest in refractive index modulation devices, such as volume phase holographic (VPH) grating, and optical waveguide devices using a refractive index difference. As an example, Patent Document 1 discloses a known phase difference measurement technique. Nowadays, the use of this technique offers a possibility to identify cancer cells and normal cells by quantified indicators.

Meanwhile, as a method for visualizing the internal structure of a biological tissue, optical coherence tomography (OCT) technique is used (e.g., see Patent Documents 2 and 3). There has also been reported a high-resolution optical coherence tomography microscope (OCM) that is achieved by increasing the resolution of this technique to allow the observation of the interior of isolated cells. Such OCT techniques can be used as a method of figuring out the stratification states of the cell sheet. In other words, by using the OCT technology, the cross-sectional shape of layered cell aggregates can be observed with a resolution at a cellular level. Thus, for example, the stratification of the corneal epithelial sheet (basal cell layer/wing cell layer/squamous cell layer) can be checked.

[Patent Document 1] Japanese Unexamined Patent Application Publication No. 2008-304456

[Patent Document 2] Japanese Unexamined Patent Application Publication No. 2003-543

[Patent Document 3] Japanese Unexamined Patent Application Publication No. 2007-101365

SUMMARY OF THE INVENTION

Problems to be Solved by the Invention

When the relationship between the internal structure and the phase difference of the cell sheet is unknown, through the conventional phase difference measurement techniques, if the phase difference of part of the cell sheet is measured relatively large, it is difficult to determine whether it is due to the difference in the thickness of the sheet or due to abnormal cells (i.e., due to the difference in the refractive index). Accordingly, to correctly interpret the measurement results of the phase difference, it is required to figure out the structure of the cell sheet as one condition.

However, the structure of the cell sheet changes in dimension at a cellular level, and sufficiently high resolution is necessitated to understand the sheet structure. That is, to determine the presence or absence of an abnormal cell and specify it, both the phase difference and the morphology (structure) have to be measured with a spatial resolution at a cellular level.

On the other hand, in OCM tests, length in the optical axis direction is defined assuming the refractive index profile of the cell sheet. The morphology of abnormal cells (cancer cells, etc.) such as those that do not satisfy this assumption cannot be accurately obtained.

It is therefore an object of the present invention to provide a technology enabling the detection of an abnormality in a sample with high accuracy.

Means of Solving the Problems

In an embodiment, an optical property measurement apparatus including a first interference optical system configured to split the optical path of light output from a first light source into a first sample optical path and a first reference optical path, scan a predetermined area of a sample with first signal light that passes through the first sample optical path, make the first signal light that has passed through the first sample optical path interfere with first reference light that has passed through the first reference optical path to generate first interference light, and detect the first interference light generated; an optical path length difference controller configured to change the optical path length difference between the first sample optical path and the first reference optical path based on a detection result of the first interference light; a change amount information acquisition unit configured to acquire change amount information indicating an amount of change in the optical path length difference made by the optical path length difference controller; a second interference optical system configured to split the optical path of light output from a second light source into a second sample optical path and a second reference optical path, scan the predetermined area with second signal light that passes through the second sample optical path, make the second signal light that has passed through the second sample optical path interfere with second reference light that has passed through the second reference optical path to generate second interference light, and detect the second interference light generated; a tomographic information acquisition unit configured to acquire tomographic information of the predetermined area based on a detection result of the second interference light; and a refractive index profile obtaining unit configured to obtain a refractive index profile in the predetermined area based on the change amount information acquired by the change amount information acquisition unit, and the tomographic information acquired by the tomographic information acquisition unit.

DETAILED DESCRIPTION

Exemplary embodiments of an optical property measurement apparatus and an optical property measurement method are described in detail below with reference to the drawings. The embodiments are applied to obtain the optical properties of any sample having a layer structure. Examples of the sample include, in addition to the cell sheet described above, optical wavelength multiplexing filters having a waveguide structure and the like.

The embodiments are intended to improve the accuracy of the detection of abnormality in a sample by combining the phase difference measurement technique as disclosed in Patent Document 1 or the like and the OCT technique as disclosed in Patent Document 2 or the like. Incidentally, the description of the documents mentioned herein can be incorporated as the contents of the following embodiments.

(Overview of Phase Difference Measurement Technique)

Described below is the overview of the phase difference measurement technique used in the embodiments. The phase difference to be measured is the one between the light that has passed through a low refractive index area and the light that has passed through a high refractive index area. Assuming that the refractive index of the low refractive index area is $n_L$, the refractive index of the high refractive index area is $n_H$, the thickness of the sample is t, and the wavelength of light is $\lambda$, then the phase difference $\Delta\phi$ can be obtained by the following equation: $\Delta\phi = 2\pi t(n_H - n_L)/\lambda_0$. Here, if the optical path length (optical distance) of light passing through the high refractive index area is changed by an amount corresponding to the phase difference $\Delta\phi$, the phase difference between both light becomes zero. Therefore, by detecting the change amount of the optical path length, the phase difference $\Delta\phi$ can be obtained. Moreover, if the thickness t of the sample is known, the refractive index difference $\Delta n = n_H - n_L$ can be obtained based on the above equation.

The phase difference measurement technique is based on this principle and detects interference light between light (first reference light) passing through an optical path (first reference optical path) having a constant optical path length and light (first signal light) passing through an optical path (first sample optical path), the length of which is affected by the optical properties of a sample, to obtain information indicating the optical properties of the sample. This information may include distribution of the phase difference, distribution of the refractive index difference, distribution of the optical path length difference on the basis of the first reference light (first reference optical path), and the like (these distributions are equivalent).

(Overview of OCT Technique)

Described below is the overview of the OCT technique used in the embodiments. The OCT is an optical measurement technique which, by detecting interference light obtained by interference between signal light (second signal light) having passed through a sample and reference light (second reference light), acquires tomographic information of the site of the sample that the second signal light has passed through. Any type of OCT may be applicable in the embodiments. Examples of OCT include swept source OCT, spectral domain OCT, and time domain OCT.

In the swept source OCT, while the wavelength of output light is swept at high speed using a wavelength-swept light source, each of measurement points (A-lines) is measured, and a series of interference light obtained thereby is detected. Then, by performing signal processing on the detection result, tomographic information of each A-line is obtained. This tomographic information represents the distribution of intensity of reflection (reflection intensity distribution) in the A-line. By arranging the tomographic information obtained for a plurality of A-lines, two-dimensional or three-dimensional tomographic information (tomographic image data) is created.

In the spectral domain OCT, a broadband light source, such as a super luminescent diode (SLD), and a spectrometer are used. Broadband light output from the broadband light source is irradiated on an A-line, a mixed light of light reflected from different depths of the A-line is detected by the spectrometer. By performing signal processing on spectra thus obtained, tomographic information indicating the reflection intensity distribution in the A-line is obtained. By arranging the tomographic information obtained for a plurality of A-lines, two-dimensional or three-dimensional tomographic information (tomographic image data) is created.

In the time domain OCT, a broadband light source and an optical path length modulator for modulating the optical path length of the optical path (second reference optical path) of the second reference light are used. The optical path length modulator includes, for example, a mirror provided on the second reference optical path and a drive mechanism (a piezoelectric element etc.) that moves the mirror in the optical axis direction. In this type of OCT, while the depth of interference is being changed by modulating the optical path length of the second reference optical path, the A-line are measured one by one with broadband light, and the intensities of reflection thereof are detected. By arranging a plurality of pieces of reflection intensity information thus obtained in the depth direction, tomographic information of the A-line can be obtained. Further, by arranging the tomographic information obtained for a plurality of A-lines, two-dimensional or three-dimensional tomographic information (tomographic image data) is created.

First Embodiment

Figure 1:
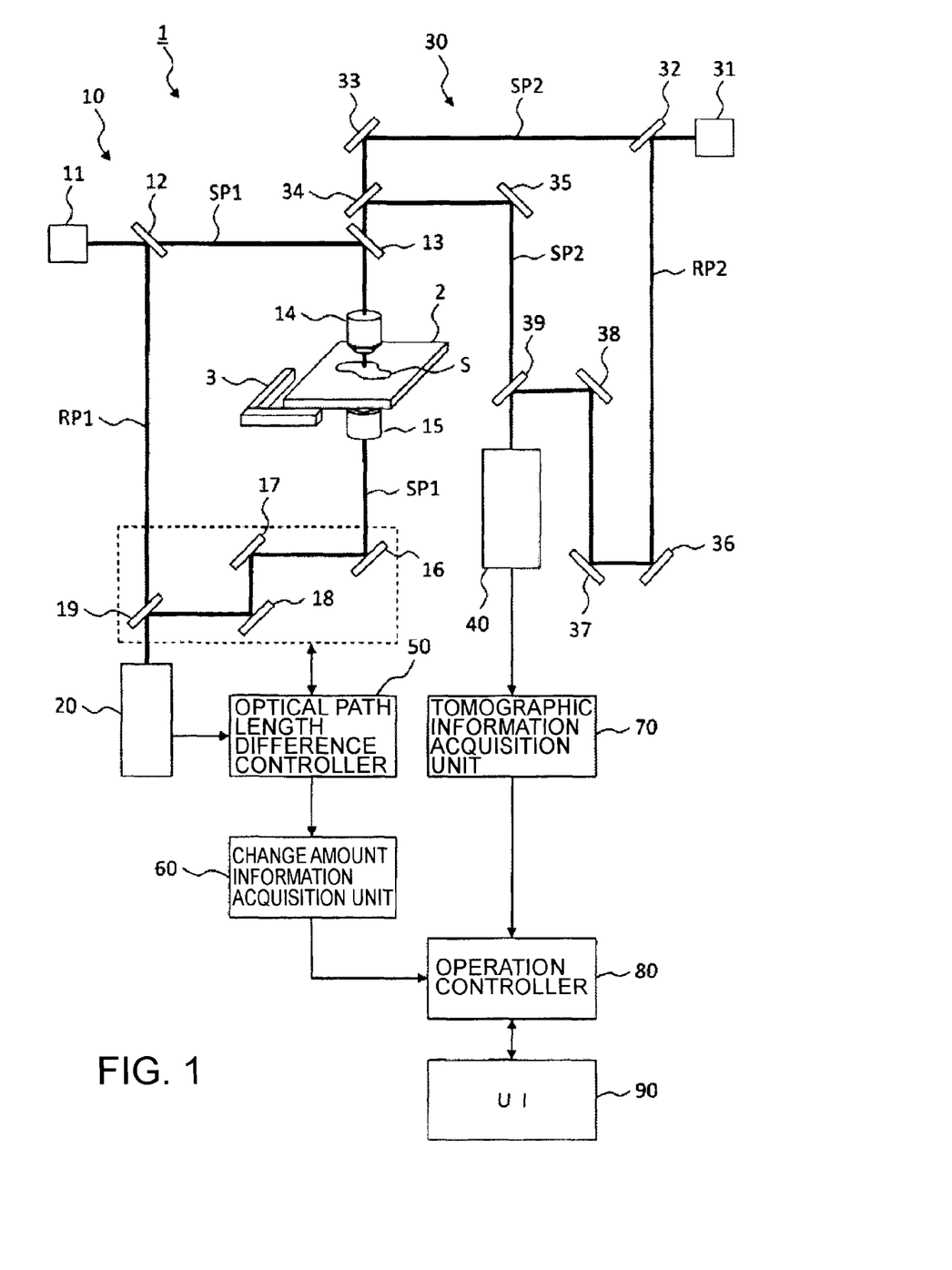
FIG. 1 is a schematic diagram illustrating an example of the configuration of an optical property measurement apparatus according to an embodiment.

FIG. 1 illustrates an optical property measurement apparatus 1 that includes a first interference optical system 10 and a second interference optical system 30. The first interference optical system 10 is used for phase difference measurement, while the second interference optical system 30 is used for OCT measurement.

Incidentally, FIG. 1 mainly illustrates an aspect of combination of the optical path of the first interference optical system 10 and the optical path of the second interference optical system 30, and does not illustrate some optical members. For example, the first interference optical system 10 is provided with a wavelength plate, a lens, and the like (not illustrated). Besides, the second interference optical system 30 is provided with an attenuator and a polarization controller, a lens (not illustrated), and the like. The first interference optical system 10 and/or the second interference optical system 30 may be configured as a fiber optic system using optical fibers.

The optical property measurement apparatus 1 measures the optical properties of a sample S placed on a stage 2. Incidentally, the sample S may be directly placed on the stage 2, or a case in which the sample S is stored may be placed on the stage 2. As an example of the latter case, a petri dish containing a cell sheet may be placed on the stage 2.

A driver 3 moves the stage 2 in a direction substantially perpendicular to the optical axis of a first sample optical path SP1. The driver 3 of this embodiment is capable of moving it in any direction in a plane substantially perpendicular to the optical axis of the first sample optical path SP1. Thereby, the sample S and the first signal light can be moved relatively and two-dimensionally.

In this embodiment, the first interference optical system 10 and the second interference optical system 30 share an objective lens 14. Therefore, the driver 3 is configured to move the stage 2 in a direction substantially perpendicular to both the optical axis of the first sample optical path SP1 and a second sample optical path SP2. With this configuration, a predetermined area of the sample S can be scanned with first signal light and second signal light. The driver 3 may be configured to be capable of moving the stage 2 in the optical axis direction of the first sample optical path SP1 etc.

The driver 3 includes, for example, a rail extending along the movable direction of the stage 2 and an actuator that outputs a driving force for moving the stage 2. The driver 3 operates under the control of an operation controller 80.

(First Interference Optical System 10)

Described below is the function of the first interference optical system 10. The first interference optical system 10 splits the optical path of light output from a first light source 11 into the first sample optical path SP1 and first reference optical path RP1. Subsequently, the first interference optical system 10 scans a predetermined area of the sample S with the first signal light passing through the first sample optical path SP1. Further, the first interference optical system 10 lets the first signal light having passed through the first sample optical path SP1 interfere with the first reference light having passed through the first reference optical path RP1 to generate first interference light. Then, the first interference optical system 10 detects the first interference light thus generated. Described below is an example of a configuration for realizing such a function.

As the first light source 11, for example, a coherent laser light source is used. The optical path of light output from the first light source 11 is split by a beam splitter 12 into the first sample optical path SP1 and the first reference optical path RP1. The beam splitter 12 may be, for example, a half mirror.

Light (first signal light) transmitted through the beam splitter 12 and guided to the first sample optical path SP1 is reflected by a beam splitter 13 formed of, for example, a dichroic mirror. The first signal light is then irradiated to the sample S through the objective lens 14. The first signal light transmitted through the sample S and the stage 2 travels through an objective lens 15 and reaches a beam splitter 19 via reflective mirrors 16, 17 and 18. The beam splitter 19 may be, for example, a half mirror.

Meanwhile, light (first reference light) reflected by the beam splitter 12 reaches the beam splitter 19 through the first reference optical path RP1.

The first signal light having passed through the first sample optical path SP1 and the first reference light having passed through the first reference optical path RP1 interfere with each other by the beam splitter 19. The interference light (first interference light) thus obtained is detected by a first detector 20. The first detector 20 outputs a detection signal indicating the intensity of the first interference light. As the first detector 20, for example, avalanche photodiode, photomultiplier tube, photodiode, CCD image sensor, CMOS image sensor, or the like may be used.

(Optical Path Length Difference Controller 50)

The optical path length difference controller 50 changes the optical path length difference between the first sample optical path SP1 and the first reference optical path RP1 based on the detection result of the first interference light obtained by the first detector 20. The optical path length difference controller 50 moves the reflective mirrors 16, 17 and 18 and the beam splitter 19 integrally, thereby changing the optical path length of the first sample optical path SP1. Hereinafter, the reflective mirrors 16, 17 and 18 and the beam splitter 19, which are moved by the optical path length difference controller 50, may sometimes be collectively referred to as "movement target". The optical path length difference controller 50 has a signal processing function (electronic circuit, processor, etc.) that processes a detection signal from the first detector 20 and a function (actuator etc.) of moving the movement target based on the processing result of the signal processing function.

In this embodiment, the optical path length difference is changed by changing the optical path length of the first sample optical path SP1; however, it may be changed by changing the optical path length of the first reference optical path RP1 or changing the optical path lengths of both.

The optical path length difference controller 50 changes the optical path length difference so that the intensity of the first interference light detected by the first detector 20 becomes a predetermined value. For this purpose, the optical path length difference controller 50 performs the same feedback control as described in Patent Document 1. The feedback control is performed as follows. The optical path length difference controller 50 acquires the difference between a detection signal from the first detector 20 and a predetermined constant voltage, and moves the movement target integrally through a low-pass filter. In that case, the optical path length difference controller 50 includes a difference circuit, a low-pass filter, and a drive mechanism. As the drive mechanism, for example, a piezoelectric element is used. This feedback control is performed in such a manner that the phase difference between the first signal light and the first reference light is always a predetermined amount. Through such feedback control, in the scanning of the sample S with the first signal light, the optical path length of the first sample optical path SP1 via the sample S is made substantially constant.

(Change Amount Information Acquisition Unit 60)

The change amount information acquisition unit 60 acquires change amount information indicating the amount of change in the optical path length difference caused by the optical path length difference controller 50. The change amount information is not limited to the change amount itself of the optical path length difference, and any information equivalent thereto may be used. In this embodiment, the change amount information acquisition unit 60 is configured to acquire change amount information indicating the amount of change in the optical path length of the first sample optical path SP1. If the optical path length difference controller 50 has the above configuration, the change amount information acquisition unit 60 detects a voltage applied to the piezoelectric element of the optical path length difference controller 50 as the change amount information indicating the amount of change in the optical path length of the first sample optical path SP1.

The change amount information acquisition unit 60 acquires the change amount information in parallel with the scanning of the sample S with the first signal light and the feedback control performed by the optical path length difference controller 50. Such integrated control is performed by the operation controller 80. Thereby, the change amount information acquisition unit 60 acquires the change amount information indicating time-series variation in the change amount of the optical path length difference. The change amount information is sent to the operation controller 80. In the above example of detecting a voltage applied to the piezoelectric element, the change amount information includes the time-series variation of the applied voltage related to scanning, i.e., the values of applied voltages corresponding to a plurality of measurement points scanned.

(Second Interference Optical System 30)

Described below is the function of the second interference optical system 30. The second interference optical system 30 splits the optical path of light output from a second light source 31 into the second sample optical path SP2 and a second reference optical path RP2. Subsequently, the second interference optical system 30 scans a predetermined area of the sample S with the second signal light passing through the second sample optical path SP2. Further, the second interference optical system 30 lets the second signal light having passed through the second sample optical path SP2 interfere with the second reference light having passed through the second reference optical path RP2 to generate second interference light. Then, the second interference optical system 30 detects the second interference light generated. Described below is an example of a configuration for realizing such a function.

As the second light source 31, a light source according to the type of OCT is used. For example, a wavelength-swept light source (wavelength tunable light source) is used for swept source OCT, and a broadband light source is used for spectral domain OCT and time domain OCT. The optical path of light output from the second light source 31 is split by a beam splitter 32 into the second sample optical path SP2 and the second reference optical path RP2. The beam splitter 32 may be, for example, a half mirror.

Light (second signal light) transmitted through the beam splitter 32 and guided to the second sample optical path SP2 is reflected by a reflective mirror 33, and is transmitted through a beam splitter 34 and then the beam splitter 13. Here, the beam splitter 13 is a dichroic mirror that reflects the output wavelength of the first light source 11 and transmits the output wavelength of the second light source 31. Through the beam splitter 13, the first sample optical path SP1 and the second sample optical path SP2 are combined together.

The second signal light is then irradiated to the sample S through the objective lens 14. The second signal light is scattered and reflected at various depths of the sample S. Backscattered light (also referred to as "second signal light") of the second signal light from the sample S travels through the objective lens 14, penetrates through the beam splitter 13, and is reflected by the beam splitter 34 and then by a reflective mirror 35, thereby reaching a beam splitter 39. The path from the beam splitter 32 to the beam splitter 39 corresponds to the second sample optical path SP2.

Meanwhile, light (second reference light) reflected by the beam splitter 32 reaches the beam splitter 39 through reflective mirrors 36, 37 and 38 arranged on the second reference optical path RP2. Incidentally, according to the principles of OCT, the second interference optical system 30 is designed such that the optical path length of the second sample optical path SP2 is to be substantially equal to the optical path length of the second reference optical path RP2.

The second signal light having passed through the second sample optical path SP2 and the second reference light having passed through the second reference optical path RP2 interfere with each other by the beam splitter 39. The interference light (second interference light) thus obtained is detected by a second detector 40. The second detector 40 has a configuration corresponding to the type of OCT. For example, a photodetector or a balanced photodetector is used for swept-source OCT and time domain OCT, and a spectrometer is used for spectral domain OCT.

(Tomographic Information Acquisition Unit 70)

The tomographic information acquisition unit 70 acquires tomographic information of a predetermined area of the sample S based on the detection result of the second interference light by the second detector 40. The predetermined area of the sample S refers to an area of the sample S that has been scanned with the second signal light. The tomographic information acquisition unit 70 performs the above processing according to the type of OCT, and generates tomographic information from the detection result of the second interference light. The tomographic information is sent to the operation controller 80.

(Operation Controller 80)

The operation controller 80 performs various types of arithmetic processing and control processing. For example, the operation controller 80 controls each part of the optical property measurement apparatus 1. Besides, the operation controller 80 has a function as a refractive index profile obtaining unit, and performs arithmetic processing described below.

The operation controller 80 obtains refractive index profile in a predetermined area of the sample S based on the change amount information acquired by the change amount information acquisition unit 60, and the tomographic information acquired by the tomographic information acquisition unit 70. The predetermined area of the sample S is all or part of the common area in areas scanned by OCT measurement and scanned by phase difference measurement. In this embodiment, for example, the same area can be scanned by phase difference measurement and OCT measurement. Such scanning may be performed simultaneously or at different times.

An example of the process for obtaining refractive index profile is described. The operation controller 80 performs the following process for each of the measurement points of the sample S that have been scanned with both the first signal light and the second signal light. In this embodiment, both the scans are performed by the movement of the stage 2, and thus measurement points in both the measurements can be naturally associated. That is, when both the scans are performed at the same time, the first interference light and the second interference light detected substantially at the same time include information of the same measurement point (A-line), and therefore, change amount information and tomographic information based on these pieces of interference light can be associated with each other. On the other hand, when both the scans are performed at different times, the position information of the stage 2 and acquired information (change amount information, tomographic information) are associated with each other in both the scans. Thereby, change amount information and tomographic information associated with (substantially) the same position information can be associated with each other.

The operation controller 80 performs the following three steps of processing for each measurement point in both the scans:

(1) calculate optical distance information in the thickness direction of the sample S at each measurement point based on change amount information acquired by the change amount information acquisition unit 60;

(2) calculate spatial distance information in the thickness direction of the sample S at each measurement point based on tomographic information acquired by the tomographic information acquisition unit 70; and (3) divide the optical distance information calculated by step (1) by the spatial distance information calculated by step (2) to obtain the refractive index of the sample S at each measurement point.

The first step of the processing is described. As described above, the change amount information includes information indicating time-series variation in the change amount of the optical path length difference. For example, upon detecting a voltage applied to the piezoelectric element, as in the above example, the change amount information includes the time-series variation of the applied voltage related to scanning, i.e., the values of applied voltages corresponding to a plurality of measurement points. The operation controller 80 converts the value of applied voltage corresponding to each measurement point into the value of the optical path length. This process is performed by obtaining the displacement of each measurement point corresponding to the applied voltage based on the characteristics of the piezoelectric element (relationship between the applied voltage and the displacement) acquired in advance. The displacement thus obtained is information indicating an optical distance in the thickness direction of the sample S at the measurement point. This information is used as the optical distance information. Here, the optical distance refers to a distance obtained by multiplying a spatial distance by the refractive index of a medium.

Figure 2:
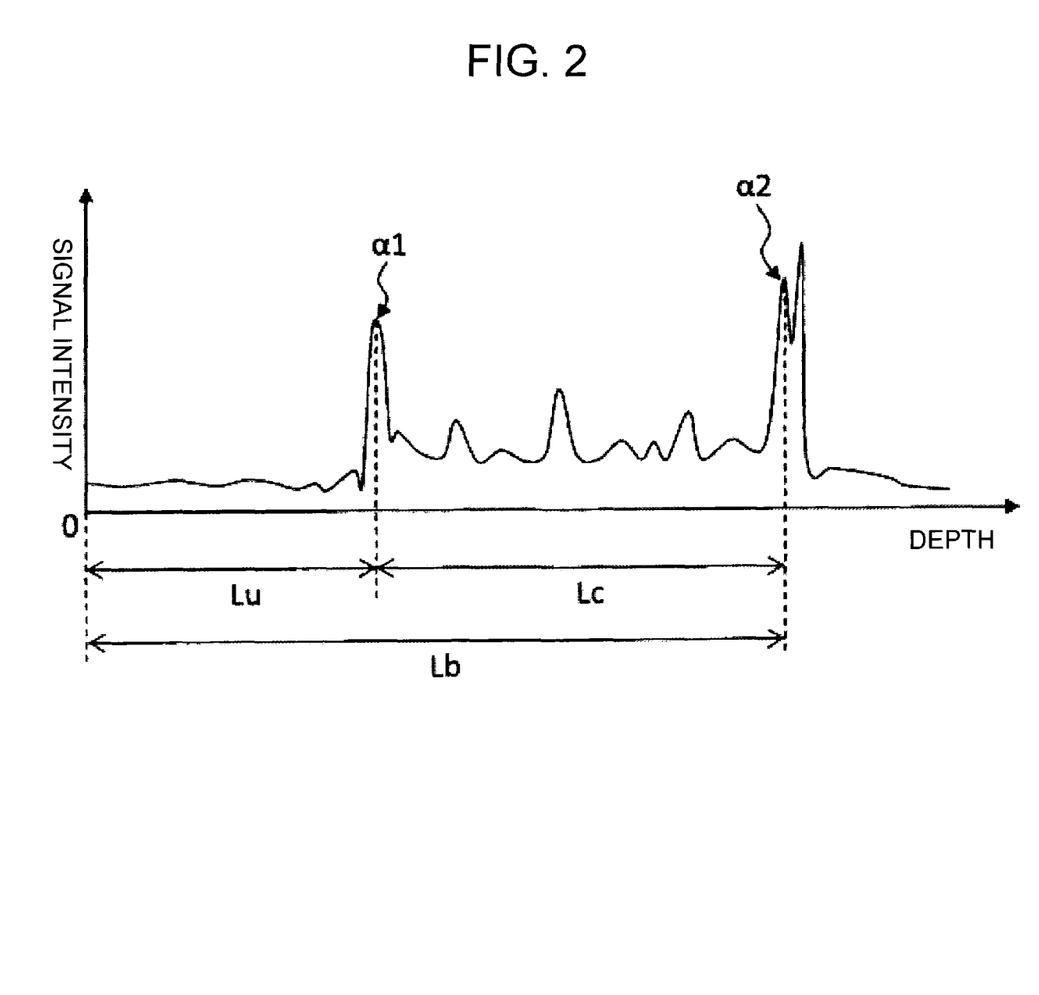
FIG. 2 is a schematic diagram for explaining an example of the operation of the optical property measurement apparatus according to the embodiment.

The second step of the processing is described. The second step of the processing includes a calculation based on the following principles. The tomographic information indicates the reflection intensity distribution (A-line profile) at each measurement point. FIG. 2 illustrates an example of the A-line profile. The horizontal axis represents the depth, and the vertical axis represents the signal intensity (i.e., intensity of reflection). On the horizontal axis, a predetermined reference depth is set at zero. The reference depth is set above the sample S (the objective lens 14 side). Peak α1 of A-line profile corresponds to the upper surface of the sample S, while peak α2 corresponds to the lower surface. The range between the peaks α1 and α2 corresponds to the reflection intensity distribution in the sample S.

There is a medium such as air and water in the space between the reference depth and the upper surface of the sample S (peak α1). The refractive index of the medium is known. Therefore, it is possible to determine the spatial distance Lu between the reference depth and the upper surface of the sample S.

It is assumed that the spatial distance Lb between the reference depth and the lower surface of the sample S (peak α2) is known. For example, when the sample S is directly placed on the stage 2, the lower surface of the sample S is in contact with the upper surface of the stage 2. Therefore, the spatial distance between the reference depth and the upper surface of the stage 2, i.e., the spatial distance Lb between the reference depth and the lower surface of the sample S can be obtained in advance. On the other hand, when the sample S is contained in a case, the sample S is placed on the placement surface of the case. Thus, based on the spatial distance between the reference depth and the upper surface of the stage 2 as well as the spatial distance between the lower end surface of the case and the placement surface, the spatial distance between the reference depth and the placement surface of the case, i.e., the spatial distance Lb between the reference depth and the lower surface of the sample S can be obtained in advance.

As described above, the spatial distance Lu between the reference depth and the upper surface of the sample S, and the spatial distance Lb between the reference depth and the lower surface of the sample S are known. Accordingly, By subtracting the spatial distance Lu from the spatial distance Lb, the spatial distance Lc in the thickness direction of the sample S at the measurement point is obtained: Lc=Lb−Lu. The spatial distance Lc indicates the thickness of the sample S at the measurement point.

Figure 3:
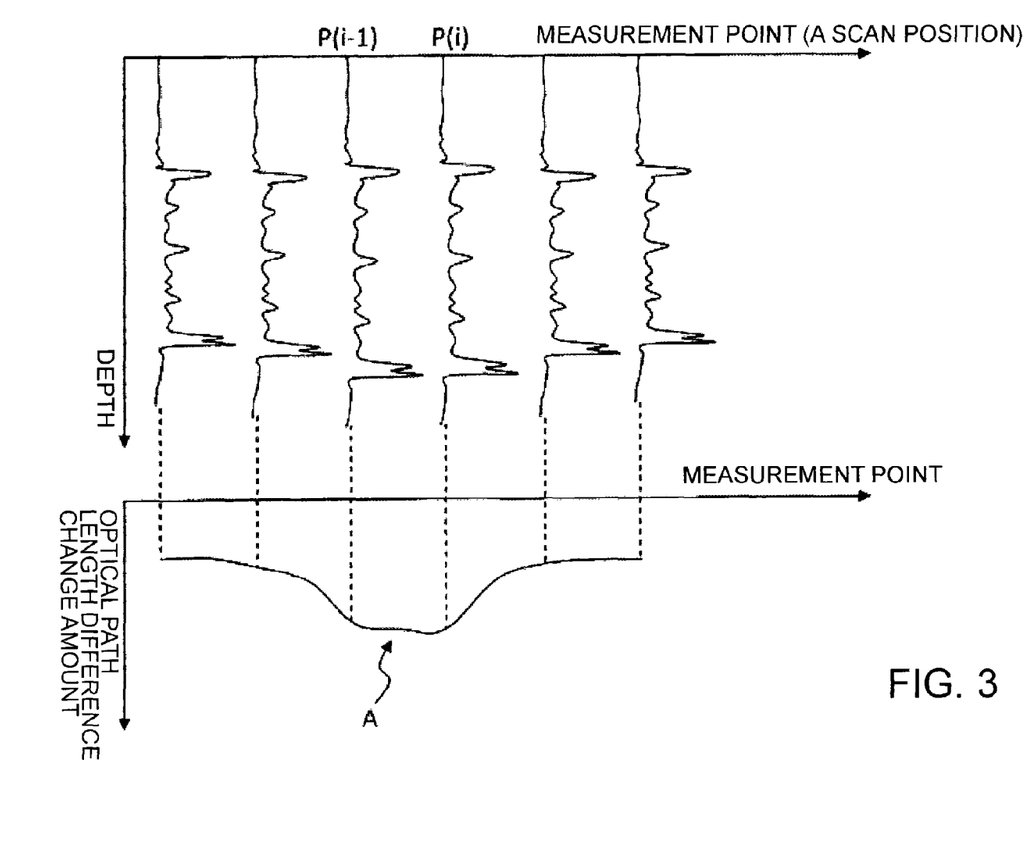
FIG. 3 is a schematic diagram for explaining an example of the operation of the optical property measurement apparatus according to the embodiment.

Thus, a plurality of values of the spatial distance Lc (thickness) corresponding to a plurality of measurement points are obtained. The same applies to the optical distance. The order is assigned to the measurement points according to the scan. The reference letters P(i) (i=1 to N) indicate the measurement points according to the order. FIG. 3 illustrates a relationship between the A-line profiles (spatial distances) corresponding to the measurement points P(i) and the optical path length difference change amounts A (optical distances).

The optical path length difference change amount A(i) at the measurement point P(i) (i=2 to N) indicates the change amount of the optical path length difference corresponding to the scan shift from the measurement point P(i−1) to the measurement point P(i). Meanwhile, the spatial distance corresponding to the scan shift from the measurement point P(i−1) to the measurement point P(i) is the difference ΔLb(i) between the spatial distance Lb(i) at the measurement point P(i) and the spatial distance Lb (i−1) at the measurement point P(i−1): ΔLb(i)=Lb(i)−Lb(i−1). The optical distance information includes a plurality of values of the optical path length difference change amount A(i) corresponding to the measurement points P(i). The spatial distance information includes a plurality of values of the difference spatial distance ΔLb(i) corresponding to the measurement points P(i).

The third step of the processing is described. The operation controller 80 obtains the refractive index of the sample S at each measurement point P(i) by dividing the optical distance information calculated in the first step by the spatial distance information calculated in the second step. To be specific, with respect to each measurement point P(i), the operation controller 80 obtains the refractive index n(i) of the sample S at the measurement point P(i) by dividing the optical path length difference change amount A(i) by the difference spatial distance ΔLb(i). Thereby, the refractive index profile n(i) at the measurement points P(i), i.e., the refractive index profile n(i) in a scanned area is obtained.

The operation controller 80 detects an abnormality in the sample S based on the information thus obtained. The abnormality detection is performed based on the optical path length difference change amount A(i), the spatial distance Lb(i), the difference spatial distance ΔLb(i), the refractive index profile n(i), and/or the like. That is, the abnormality detection is performed based on information indicating the internal structure of the sample S and information indicating the optical properties thereof.

As a specific example, first, the operation controller 80 specifies the measurement point P(i) where the refractive index n(i) indicates an abnormal value based on a predetermined threshold. Next, for each measurement point P(i), the operation controller 80 determines whether structural features (morphological characteristics) are present. Examples of the determination as to the structural features include: whether the spatial distance Lb(i) is abnormal (i.e., whether the thickness is abnormal); whether the difference spatial distance ΔLb(i), ΔLb (i+1), and the like is abnormal (i.e., whether there has been a steep change in the thickness); whether any abnormality is detected from an OCT image (whether there is an abnormality in the thickness, shape, etc. of a particular layer, or the like). The operation controller 80 specifies the abnormal portion of the sample S based on an abnormality specified from the refractive index n(i) and the structural features.

(User Interface 90)

The user interface 90 includes a display and an operation unit (not illustrated). The display displays various types of information under the control of the operation controller 80. Examples of the information displayed include the result of the abnormality determination, information obtained by phase difference measurement and OCT measurement, a tomographic image based on information obtained by OCT measurement, information about the sample S, and the like. The operation unit is used for the operation of the optical property measurement apparatus 1, input of various types of information, and the like.

(Actions and Effects)

Described below are the actions and effects of the optical property measurement apparatus 1.

The optical property measurement apparatus 1 includes the first interference optical system 10, the optical path length difference controller 50, the change amount information acquisition unit 60, the second interference optical system 30, the tomographic information acquisition unit 70, and the operation controller 80. The first interference optical system 10, the optical path length difference controller 50, and the change amount information acquisition unit 60 perform the phase difference measurement of the sample S. The second interference optical system 30 and the tomographic information acquisition unit 70 perform the OCT measurement of the sample S.

The first interference optical system 10 performs the following operations: splitting the optical path of light output from the first light source 11 into the first sample optical path SP1 and the first reference optical path; scanning a predetermined area of the sample S with the first signal light that passes through the first sample optical path SP1; making the first signal light that has passed through the first sample optical path SP1 interfere with the first reference light that has passed through the first reference optical path RP1 to generate the first interference light; and detecting the first interference light generated.

The optical path length difference controller 50 changes the optical path length difference between the first sample optical path SP1 and the first reference optical path RP1 based on the detection result of the first interference light obtained by the first interference optical system 10.

The change amount information acquisition unit 60 obtains the change amount information indicating the amount of change in the optical path length difference made by the optical path length difference controller 50.

The second interference optical system 30 performs the following operations: splitting the optical path of light output from the second light source 31 into the second sample optical path SP2 and the second reference optical path RP2; scanning a predetermined area of the sample S with the second signal light that passes through the second sample optical path SP2; making the second signal light that has passed through the second sample optical path SP2 interfere with the second reference light that has passed through the second reference optical path RP2 to generate the second interference light; and detecting the second interference light generated.

The tomographic information acquisition unit 70 acquires tomographic information of the predetermined area of the sample S based on the detection result of the second interference light obtained by the second interference optical system 30.

The operation controller 80 obtains a refractive index profile in the predetermined area of the sample S based on the change amount information acquired by the change amount information acquisition unit 60, and the tomographic information acquired by the tomographic information acquisition unit 70. The operation controller 80 that performs this process corresponds to the "refractive index profile obtaining unit".

In this embodiment, the operation controller 80 as the refractive index profile obtaining unit is configured to perform the following operations. For each measurement point that is measured by the scanning of the first signal light and the second signal light, the operation controller 80 calculates the optical distance in the thickness direction of the sample S at the measurement point based on the change amount information acquired by the change amount information acquisition unit 60. In addition, the operation controller 80 calculates the spatial distance in the thickness direction of the sample S at the measurement point based on the tomographic information acquired by the tomographic information acquisition unit 70. Further, the operation controller 80 obtains the refractive index of the sample S at the measurement point by dividing the optical distance by the spatial distance.

In this embodiment, the first interference optical system 10 and the second interference optical system 30 are configured as follows. The first sample optical path SP1 and the second sample optical path SP2 are combined by a combining member (the beam splitter 13). Between the combining member (the beam splitter 13) and the sample S is arranged the objective lens 14. The first interference optical system 10 is configured to irradiate the sample S with the first signal light through the objective lens 14. The second interference optical system 30 is configured to irradiate the sample S with the second signal light through the objective lens 14. That is, the first interference optical system 10 and the second interference optical system 30 may be configured to share the objective lens 14.

The optical property measurement apparatus 1 of this embodiment includes a placement unit (the stage 2) and the driver 3. The sample S is placed on the placement unit (the stage 2). The driver 3 performs scanning of the sample S with the first signal light and the second signal light by moving the placement unit (the stage 2) in a direction substantially perpendicular to both the optical axis of the first sample optical path SP1 and the optical axis of the second sample optical path SP2.

In this embodiment, the type of OCT measurement is arbitrary. In the case of swept source OCT, the second light source 31 is a wavelength-swept light source, and the tomographic information acquisition unit 70 acquires tomographic information based on the detection result of the second interference light obtained by the second interference optical system 30 along with a sweep of wavelengths by the wavelength-swept light source. In the case of spectral domain OCT, the second light source 31 is a broad band light source, the second interference optical system 30 includes a spectrometer (the second detector 40) that detects the spectra of the second interference light, and the tomographic information acquisition unit 70 acquires tomographic information based on the detection result of the spectra obtained by the spectrometer (the second detector 40). In the case of time-domain OCT, the second light source 31 is a broad band light source, the second interference optical system 30 includes an optical path length modulator that modulates the optical path length of the second reference optical path RP2, and the tomographic information acquisition unit 70 acquires the tomographic information based on the detection result of the second interference light obtained by the second interference optical system 30 along with the modulation of the optical path length of the second reference optical path RP2. The optical path length modulator includes, for example, a piezoelectric element to move the reflective mirrors 36 and 37 integrally. The operation controller 80 applies voltage to the piezoelectric element.

With the optical property measurement apparatus 1, based on the results of both the optical property measurement (refractive index measurement, phase difference distribution measurement) and structure measurement (OCT measurement) of the sample S, the abnormality detection of the sample S can be performed with high accuracy. For example, when the sample S is a cell sheet, it cannot be determined by the conventional phase difference measurement techniques whether the detected abnormality is due to an abnormality in the optical properties caused by the mutation of cells or an abnormality in the structure of the sample S (such as thickness variation, etc.). On the other hand, according to this embodiment, it is possible to make such determination.

Second Embodiment

Figure 4:
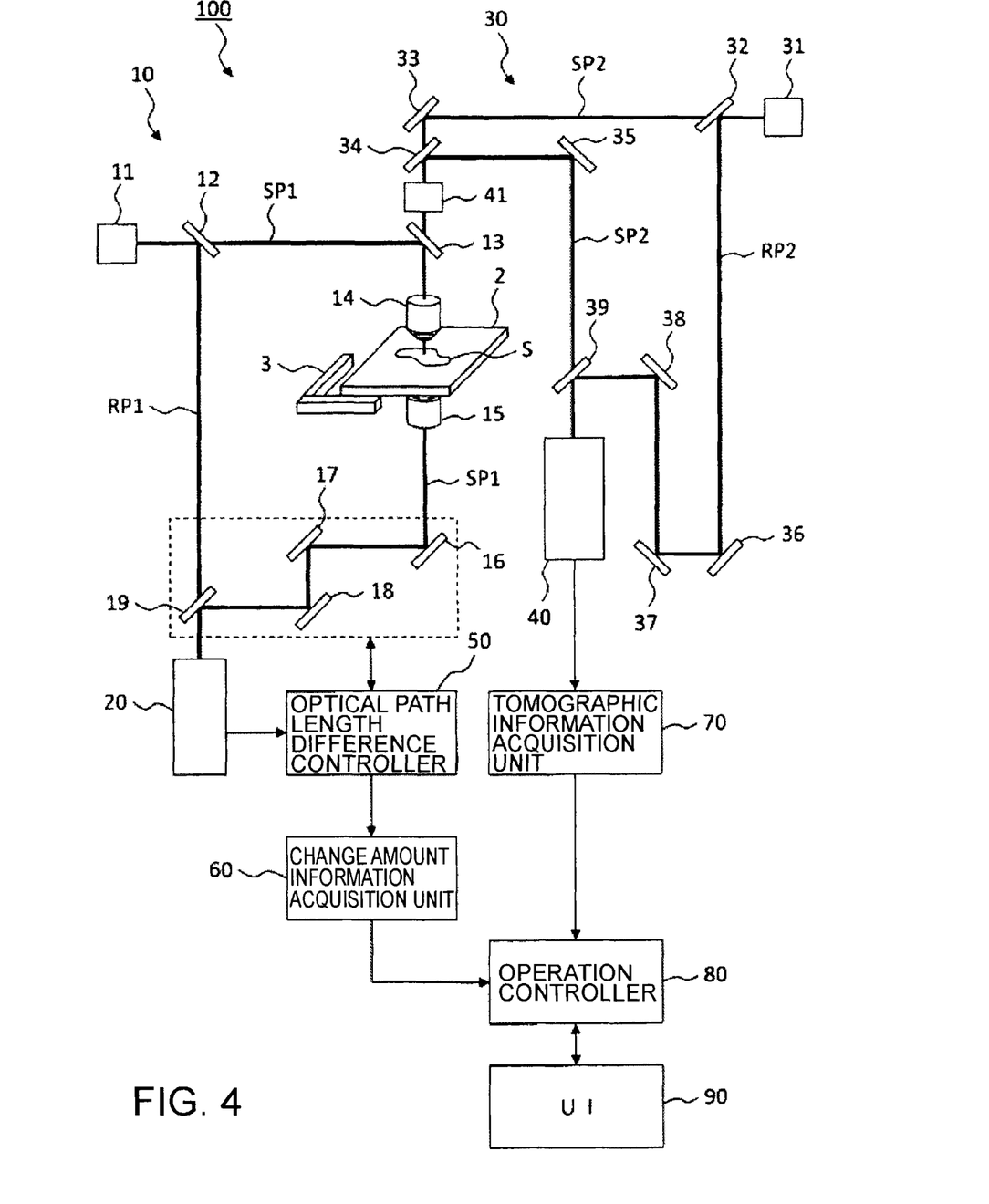
FIG. 4 is a schematic diagram illustrating an example of the configuration of the optical property measurement apparatus according to the embodiment.

FIG. 4 illustrates an optical property measurement apparatus 100 of this embodiment. The optical property measurement apparatus 100 includes the first interference optical system 10 and the second interference optical system 30 similar to those of the first embodiment. This embodiment is different from the first embodiment in that the second interference optical system 30 is provided with a galvanometer scanner 41. The optical path length difference controller 50, the change amount information acquisition unit 60, the tomographic information acquisition unit 70, the operation controller 80, and the user interface 90 are the same as those of the first embodiment, and therefore, a detailed description is omitted.

The galvanometer scanner 41 is arranged on the second sample optical path SP2, and performs the scanning of the sample S by deflecting the second signal light directed toward the sample S. The galvanometer scanner 41 is an example of a deflecting optical system. The galvanometer scanner 41 includes one or two reflective mirrors and a drive mechanism that changes the orientation of each reflective mirror. The drive mechanism operates under the control of the operation controller 80.

Scan for phase difference measurement by means of the first interference optical system 10 is implemented by the movement of the stage 2 by the driver 3, and scan for OCT measurement by means of the second interference optical system 30 is performed by the galvanometer scanner 41. That is, in this embodiment, the scans of the two measurements are performed independently of each other.

With the optical property measurement apparatus 100 of this embodiment, as in the first embodiment, based on the results of both the optical property measurement and structure measurement of the sample S, the abnormality detection of the sample S can be performed with high accuracy.

The deflecting optical system is not limited to the galvanometer scanner. For example, an optical device such as a polygon mirror may be used as the deflecting optical system.

The first interference optical system 10 may be provided with a deflecting optical system. In this case, the deflecting optical system is arranged on the first sample optical path SP1, and performs the scanning of the sample S by deflecting the first signal light directed toward the sample S. If both the first interference optical system 10 and the second interference optical system 30 are provided with the deflecting optical system, the driver 3 for moving the stage 2 is not necessary. Alternatively, the scanning of the first signal light and/or the second signal light may be performed by interlock control of the driver 3 and the deflecting optical system.

Third Embodiment

Figure 5:
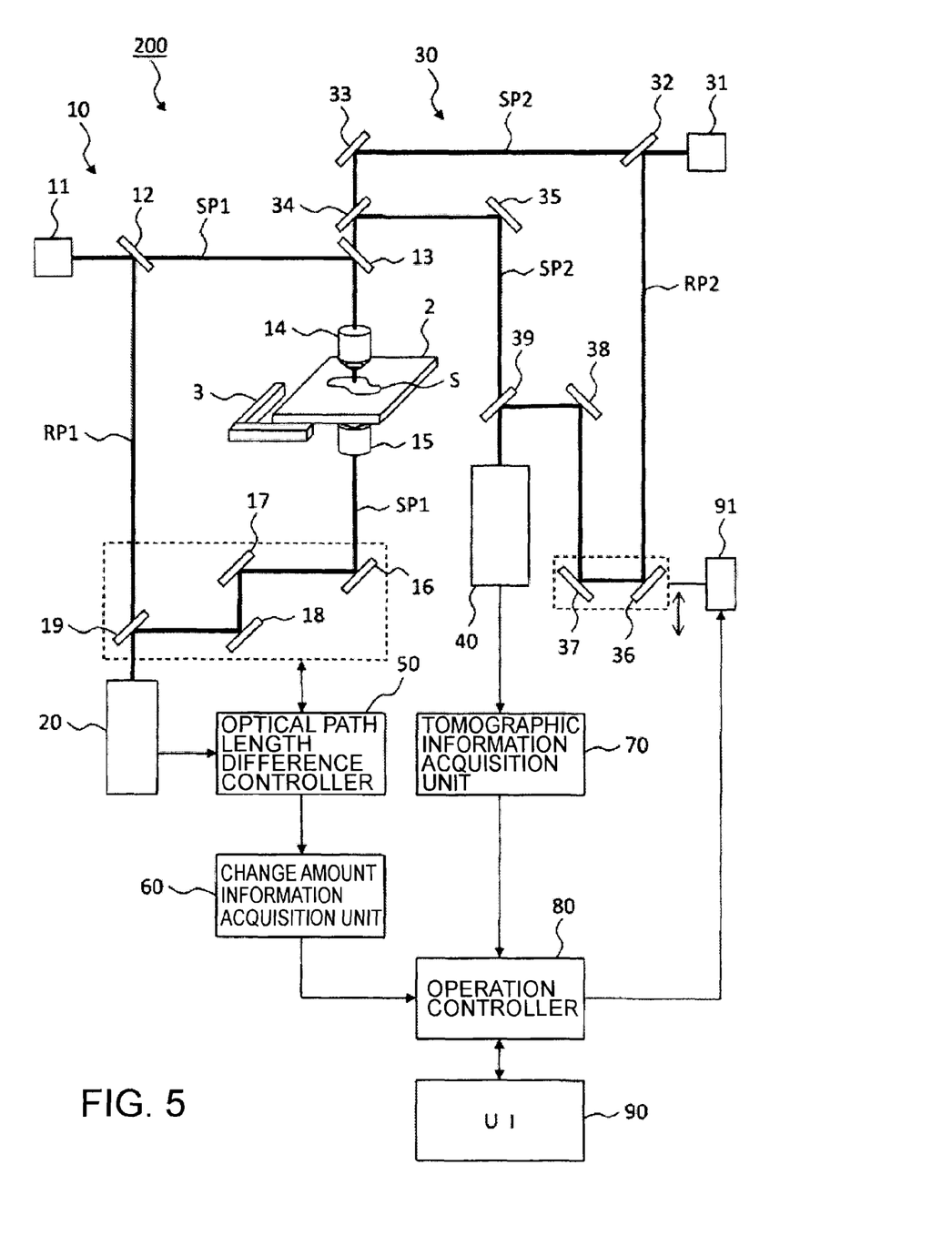
FIG. 5 is a schematic diagram illustrating an example of the configuration of the optical property measurement apparatus according to the embodiment.

FIG. 5 illustrates an optical property measurement apparatus 200 of this embodiment. The optical property measurement apparatus 200 includes the first interference optical system 10 and the second interference optical system 30 similar to those of the first embodiment. This embodiment is different from the first embodiment in that the optical path length changing unit configured to change the optical path length of the second reference optical path RP2 is arranged in the second interference optical system 30. The optical path length difference controller 50, the change amount information acquisition unit 60, the tomographic information acquisition unit 70, the operation controller 80, and the user interface 90 are the same as those of the first embodiment, and therefore, a detailed description is omitted.

The optical path length changing unit includes, for example, a drive mechanism 91 that moves the reflective mirrors 37 and 38 in the direction indicated by a double-headed arrow illustrated in FIG. 5. The drive mechanism 91 operates under the control of the operation controller 80. The drive mechanism 91 is used to change the reference depth, which has been described with reference to FIG. 2.

If the thickness of the sample S is indeterminate like a cell sheet, it may be required to change the reference depth. In OCT measurement, at the position of the optical path length of the second sample optical path SP2 that match the optical path length of the second reference optical path RP2, interference sensitivity is the maximum. Therefore, to perform OCT measurement with high sensitivity, it is necessary to adjust the optical path length difference between the second sample optical path SP2 and the second reference optical path RP2 according to the thickness of the sample S. In this embodiment, the optical path length of the second reference optical path RP2 is changed to adjust the optical path length difference. Incidentally, the optical path length of the second sample optical path SP2 may be changed, and also the optical path lengths of the both may be changed.

With the optical property measurement apparatus 200 of this embodiment, the abnormality detection of the sample S can be performed with high accuracy regardless of the thickness of the sample S.

Fourth Embodiment

In the above embodiments, the light source for phase difference measurement (the first light source 11) and the light source for OCT measurement (the second light source 31) are provided separately. This embodiment describes a configuration in which phase difference measurement and OCT measurement are performed by using a common light source. As the common light source, a wavelength-swept light source is used. Light of a predetermined wavelength is used without wavelength sweeping in phase difference measurement, while wavelength sweeping is performed in OCT measurement.

Figure 6:
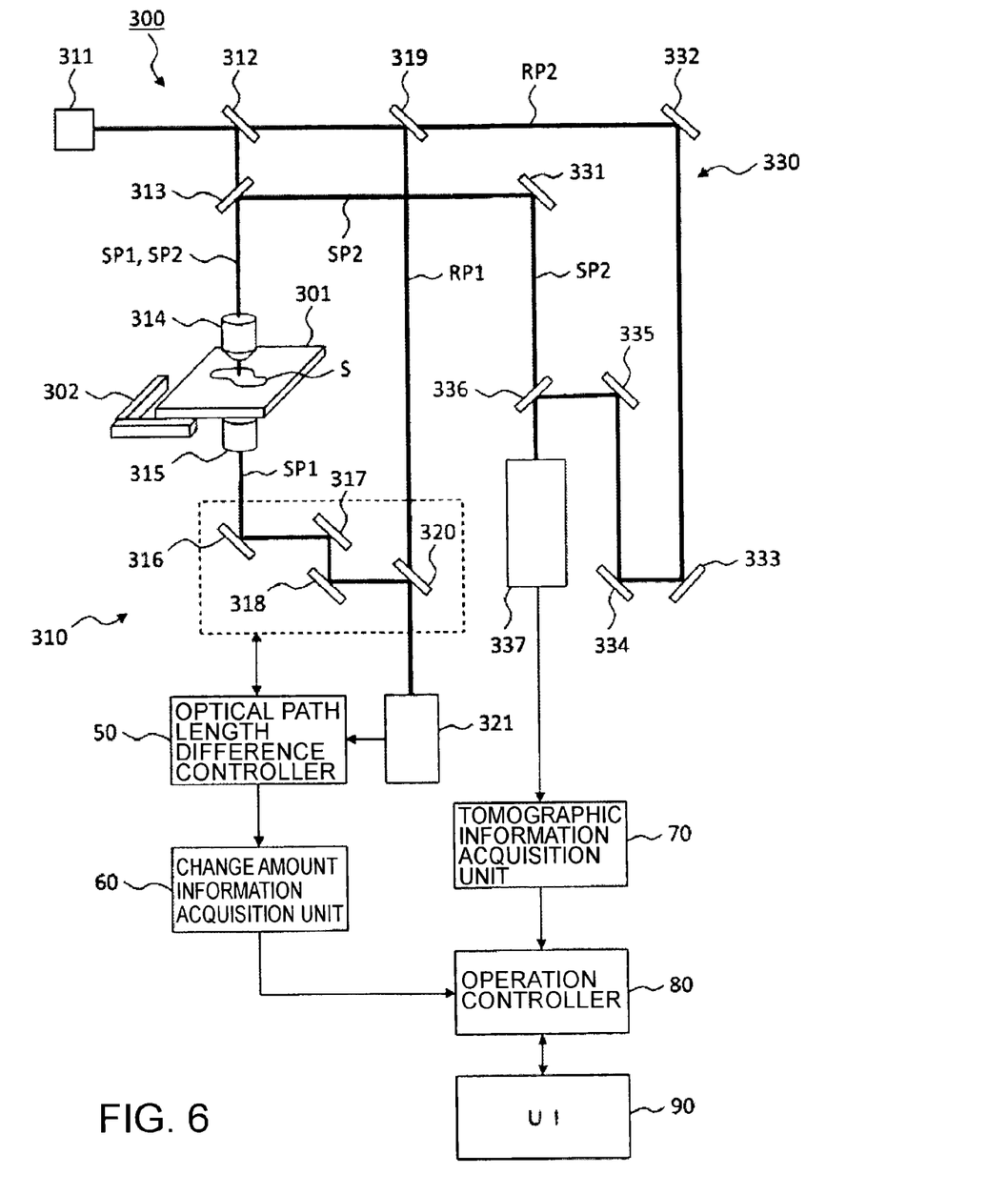
FIG. 6 is a schematic diagram illustrating an example of the configuration of the optical property measurement apparatus according to the embodiment.

FIG. 6 illustrates an optical property measurement apparatus 300 of this embodiment. The optical property measurement apparatus 300 includes a first interference optical system 310 and a second interference optical system 330. The first interference optical system 310 and the second interference optical system 330 share a part of the optical members. The optical path length difference controller 50, the change amount information acquisition unit 60, the tomographic information acquisition unit 70, the operation controller 80, and the user interface 90 are the same as those of the first embodiment, and therefore, a detailed description is omitted.

The first interference optical system 310 is described below. The optical path of light output from a light source 311 as a first light source is split by a beam splitter 312 into the first sample optical path SP1 and the first reference optical path RP1. The beam splitter 312 may be, for example, a half mirror.

Light (first signal light) reflected by the beam splitter 12 and guided to the first sample optical path SP1 is transmitted through a beam splitter 313 (such as a half mirror), and is irradiated to the sample S via an objective lens 314. The first signal light transmitted through the sample S and the stage 2 travels through an objective lens 315 and reaches a beam splitter 320 via reflective mirrors 316, 317 and 318. The beam splitter 320 may be, for example, a half mirror. The reflective mirrors 316, 317 and 318 as well as the beam splitter 320 are integrally moved by the optical path length difference controller 50.

Meanwhile, light (first reference light) transmitted through the beam splitter 312 is reflected by a beam splitter 319 (such as a half mirror), and reaches the beam splitter 320 via the first reference optical path RP1.

The first signal light having passed through the first sample optical path SP1 and the first reference light having passed through the first reference optical path RP1 interfere with each other by the beam splitter 320. The interference light (first interference light) thus obtained is detected by a first detector 321. The first detector 321 outputs a detection signal indicating the intensity of the first interference light.

The second interference optical system 330 is described below. The optical path of light output from the light source 311 as a second light source is split by the beam splitter 312 into the second sample optical path SP2 and the second reference optical path RP2.

Light (second signal light) reflected by the beam splitter 312 and guided to the second sample optical path SP2 is transmitted through the beam splitter 313 and is irradiated to the sample S via the objective lens 314. Backscattered light (also referred to as "second signal light") of the second signal light from the sample S travels through the objective lens 314, and is reflected by the beam splitter 313 and then by a reflective mirror 331, thereby reaching a beam splitter 336.

Meanwhile, light (second reference light) transmitted through the beam splitter 312 reaches the beam splitter 336 through the second reference optical path RP2. That is, the second reference light is transmitted through the beam splitter 319, and is reflected on reflective mirrors 332, 333, 334 and 335, and reaches the beam splitter 336.

The second signal light having passed through the second sample optical path SP2 and the second reference light having passed through the second reference optical path RP2 interfere with each other by the beam splitter 336. The interference light (second interference light) thus obtained is detected by a second detector 337 having a configuration according to the type of OCT.

In the optical property measurement apparatus 300 of this embodiment, the same light source 311 serves as the first light source and the second light source. The first interference optical system 310 and the second interference optical system 330 of the optical property measurement apparatus 300 include a splitting optical system configured to split the optical path of light output from the same light source 311 into the first sample optical path SP1, the first reference optical path RP1, the second sample optical path SP2, and the second reference optical path RP2. The splitting optical system includes the beam splitters 312 and 319.

With this configuration, both the measurements can be performed by a single light source. Thus, the abnormality detection of the sample S can be performed with high accuracy along with the simplification of the optical system.

Incidentally, it is possible to apply the following configuration according to the type of OCT measurement. In the case of spectral domain OCT and time domain OCT, a low-coherent broadband light source is used. Accordingly, an interference signal is obtained only at the position where the optical path length of the second sample optical path SP2 substantially matches that of the second reference optical path RP2. Therefore, by using the optical path length changing unit (not illustrated) described in the third embodiment, the process of matching the optical path length of the second sample optical path SP2 with that of the second reference optical path RP2 may be performed prior to measurement.

In the case of swept source OCT, a wavelength-swept light source with a longer coherence length is used, and the first and second light sources can be easily shared. However, it is difficult to perform phase difference measurement performed with a fixed wavelength simultaneously with OCT measurement performed while the wavelength is being swept by the same light source. Therefore, there is a need for control to perform phase difference measurement and OCT measurement in a time-division manner. For example, such control may be realized by alternately repeating: the operation of performing phase difference measurement with a fixed wavelength and OCT measurement with swept wavelengths for one measurement point; and the operation of switching the measurement point to another one by moving the stage 2. Alternatively, the control may be performed such that, after phase difference measurement (or OCT measurement) is performed for a plurality of measurement points, OCT measurement (or phase difference measurement) is performed for these measurement points.

Fifth Embodiment

In this embodiment, a description is given of an optical property measurement apparatus 400 configured to perform OCT measurement from both the upper and lower directions of the sample S.

Figure 7:
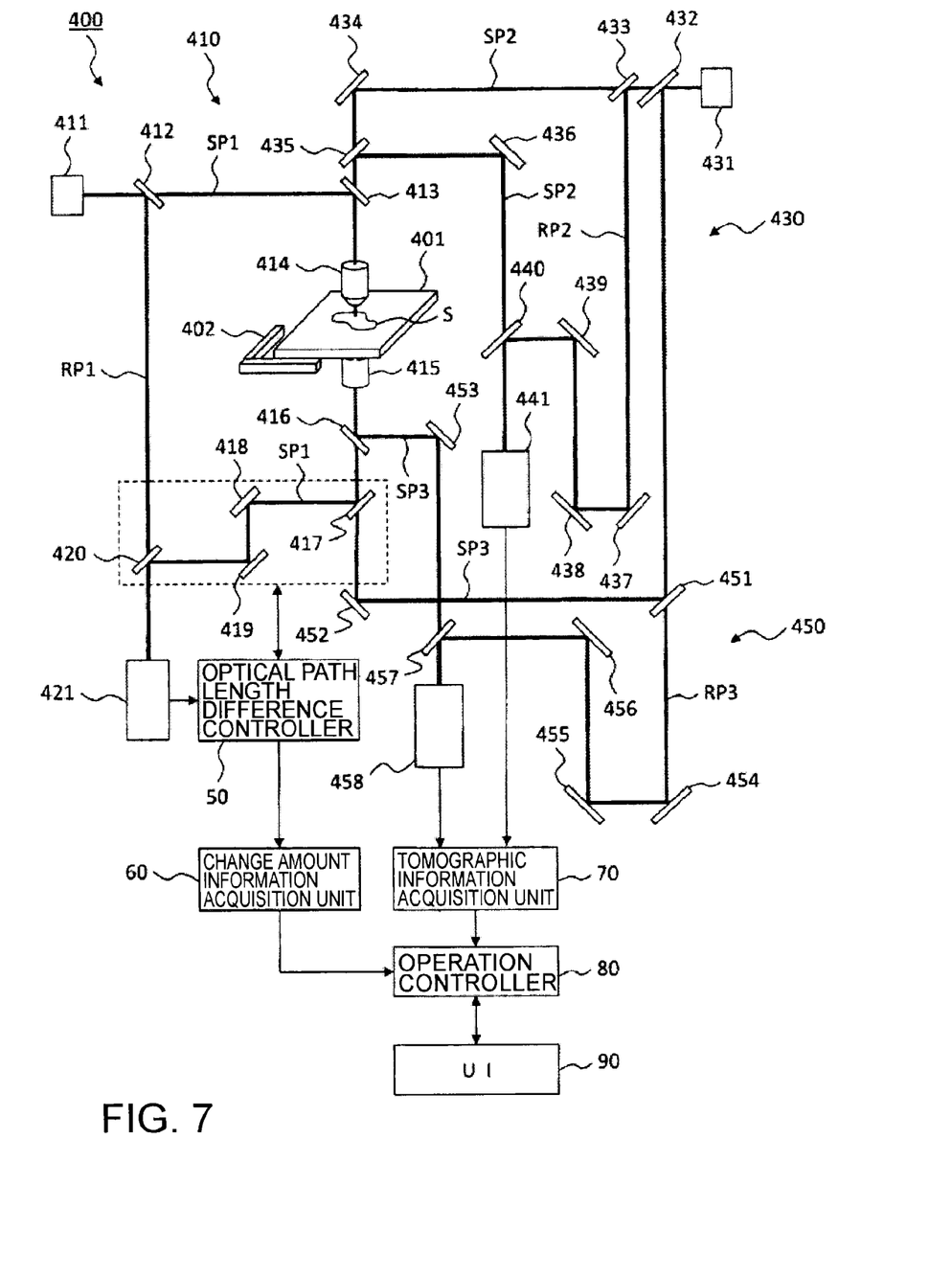
FIG. 7 is a schematic diagram illustrating an example of the configuration of the optical property measurement apparatus according to the embodiment.

FIG. 7 illustrates the optical property measurement apparatus 400 of this embodiment. The optical property measurement apparatus 400 includes a first interference optical system 410, a second interference optical system 430, and a third interference optical system 450.

The first interference optical system 410 is described below. The first interference optical system 410 is used for phase difference measurement. The optical path of light output from a first light source 411 is split by a beam splitter 412 into the first sample optical path SP1 and the first reference optical path RP1. The beam splitter 412 may be, for example, a half mirror.

Light (first signal light) transmitted through the beam splitter 412 and guided to the first sample optical path SP1 is reflected by a beam splitter 413 formed of, for example, a dichroic mirror. Further, the first signal light is irradiated to the sample S via an objective lens 414. The first signal light transmitted through the sample S and the stage 2 travels through an objective lens 415, and is transmitted through a beam splitter 416, thereby reaching a beam splitter 417. The beam splitters 416 and 417 may be, for example, dichroic mirrors. The first signal light is reflected by the beam splitter 417 and reaches a beam splitter 420 via reflective mirrors 418 and 419. The beam splitter 420 may be, for example, a half mirror. The optical path length difference controller 50 integrally moves the beam splitter 417, the reflective mirrors 418 and 419, and the beam splitter 420 to change the optical path length of the first sample optical path SP1.

Meanwhile, light (first reference light) reflected by the beam splitter 412 reaches the beam splitter 420 via the first reference optical path RP1.

The first signal light having passed through the first sample optical path SP1 and the first reference light having passed through the first reference optical path RP1 interfere with each other by the beam splitter 420. The interference light (first interference light) thus obtained is detected by a first detector 421. The first detector 421 outputs a detection signal indicating the intensity of the first interference light.

The second interference optical system 430 is described below. The second interference optical system 430 is used for OCT measurement from above the sample S (the objective lens 414 side). The optical path of light output from a second light source 431 is split by a beam splitter 432 into two. The beam splitter 432 may be, for example, a half mirror. Here, light transmitted through the beam splitter 432 is used for OCT measurement from above the sample S. On the other hand, light reflected by the beam splitter 432 is used for OCT measurement from below the sample S.

The light transmitted through the beam splitter 432 is split by a beam splitter 433 into the second sample optical path SP2 and the second reference optical path RP2. The beam splitter 433 may be, for example, a half mirror.

Light (second signal light) transmitted through the beam splitter 433 and guided to the second sample optical path SP2 is reflected by a reflective mirror 434, and is transmitted through a beam splitter 435 and the beam splitter 413. The second signal light is then irradiated to the sample S through the objective lens 414. Backscattered light (also referred to as "second signal light") of the second signal light from the sample S travels through the objective lens 414, and is transmitted through the beam splitter 413 and reflected by the beam splitter 435 and then by a reflective mirror 436, thereby reaching a beam splitter 440.

Meanwhile, light (second reference light) reflected by the beam splitter 433 reaches the beam splitter 440 via reflective mirrors 437, 438 and 439 arranged on the second reference optical path RP2.

The second signal light having passed through the second sample optical path SP2 and the second reference light having passed through the second reference optical path RP2 interfere with each other by the beam splitter 440. The interference light (second interference light) thus obtained is detected by a second detector 441. The second detector 441 has a configuration according to the type of OCT.

The third interference optical system 450 is described below. The third interference optical system 450 is used for OCT measurement from below of the sample S (the objective lens 415 side). The optical path of light output from the second light source 431 and reflected by the beam splitter 432 is split by a beam splitter 451 into a third sample optical path SP3 and a third reference optical path RP3. The beam splitter 451 may be, for example, a half mirror.

Light (third signal light) reflected by the beam splitter 451 and guided to the third sample optical path SP3 is reflected by a reflective mirror 452, and transmitted through the beam splitters 417 and 413. The third signal light is then irradiated to the sample S through the objective lens 415. Backscattered light (also referred to as "second signal light") of the third signal light from the sample S travels through the objective lens 415, and is reflected by the beam splitter 416 and then by a reflective mirror 453, thereby reaching a beam splitter 457.

Meanwhile, light (third reference light) transmitted through the beam splitter 451 reaches the beam splitter 457 via reflective mirrors 454, 455 and 456 arranged on the third reference optical path RP3.

The third signal light having passed through the third sample optical path SP3 and the third reference light having passed through the third reference optical path RP3 interfere with each other by the beam splitter 457. The interference light (third interference light) thus obtained is detected by a third detector 458. The third detector 458 has the same configuration as the second detector 441.

The tomographic information acquisition unit 70 of this embodiment acquires tomographic information (first tomographic information) of a predetermined area of the sample S based on the detection result of the second interference light obtained by the second detector 441, and also acquires tomographic information (second tomographic information) of the predetermined area based on the detection result of the third interference light obtained by the third detector 458.

The operation controller 80 (the refractive index profile obtaining unit) of this embodiment obtains a refractive index profile in the predetermined area of the sample S based on change amount information acquired by the change amount information acquisition unit 60, and the first tomographic information and the second tomographic information acquired by the tomographic information acquisition unit 70. Further, the operation controller 80 detects an abnormality in the sample based on the various types of information acquired.

By performing OCT measurement from both the upper and lower directions of the sample S, the operation controller 80 is capable of performing the following processing. As described above, the operation controller 80 can find the position of the upper surface of the sample S based on the first tomographic information. Described below is an example of this process.

It is assumed that reference depth on the upper surface side of the sample S (first reference depth) and that on the lower surface side (second reference depth) are set in advance. Incidentally, the second reference depth is set below the lower surface of the sample S. The distance between the objective lenses 414 and 415 is set in advance. The first reference depth is set as, for example, the distance from the objective lens 414, or a position relative to the stage 2. Similarly, the second reference depth is set as, for example, the distance from the objective lens 415, or a position relative to the stage 2.

The operation controller 80 obtains, for each measurement point (that is, for each A-line), the position of the upper surface of the sample S with respect to the first reference depth set in advance based on the first tomographic information. This process can be performed, for example, based on the distance between the objective lens 414 and the first reference depth, and on the spatial distance Lu illustrated in FIG. 2. Thus, the positions of the upper surface of the sample S is obtained for a plurality of measurement points. Similarly, the operation controller 80 obtains the positions of the lower surface of the sample S based on the second tomographic information for a plurality of measurement points.

The objective lenses 414 and 415 are arranged coaxially. Besides, OCT measurements from the upper and lower directions of the sample S can be performed simultaneously. Accordingly, a plurality of measurement points in the first tomographic information and those in the second tomographic information can be associated in one-to-one correspondence. The operation controller 80 can determine the thickness of the sample S along the A-line based on the upper surface position and the lower surface position of the sample S at the corresponding measurement points. Thus, the thickness distribution of the sample S in an area where OCT measurement has been performed is obtained. The operation controller 80 that performs this process corresponds to "thickness distribution obtaining unit". The operation controller 80 can obtain the refractive index profile of the sample S based on the change amount information (indicating the optical properties of the sample S) acquired by the change amount information acquisition unit 60, and the thickness distribution of the sample S (indicating the morphology and structure of the sample S).

As described above, the optical property measurement apparatus 400 of this embodiment has the following configuration. The optical property measurement apparatus 400 includes the beam splitter 432 (splitter) configured to split the optical path of light output from the second light source 431 into two optical paths.

The second interference optical system 430 splits one of the optical paths obtained by the beam splitter 432 into the second sample optical path SP2 and the second reference optical path RP3.

The other of the optical paths contributes to the third interference optical system 450. The third interference optical system 450 splits the other optical path obtained by the beam splitter 432 into the third sample optical path SP3 and the third reference optical path RP3. The third interference optical system 450 scans the sample S from the opposite direction to the second signal light with the third signal light passing through the third sample optical path SP3. The third interference optical system 450 lets the third signal light having passed through the third sample optical path SP3 interfere with the third reference light having passed through the third reference optical path RP3 to generate third interference light. Then, the third interference optical system 450 detects the third interference light generated.

The tomographic information acquisition unit 70 acquires tomographic information on a predetermined area of the sample S based on the detection result of the second interference light, and also acquires another tomographic information on the predetermined area based on the detection result of the third interference light. The operation controller 80 (the refractive index profile obtaining unit) obtains a refractive index profile in the predetermined area based on the change amount information acquired by the change amount information acquisition unit 60, and the two pieces of tomographic information acquired by the tomographic information acquisition unit 70.

The operation controller 80 as the refractive index profile obtaining unit may include the thickness distribution obtaining unit. The thickness distribution obtaining unit obtains thickness distribution in the predetermined area of the sample S based on the two pieces of tomographic information obtained by the tomographic information acquisition unit 70. Further, the operation controller 80 obtains a refractive index profile based on the change amount information and the thickness distribution.

According to this embodiment, the upper surface position and the lower surface position of the sample S, and the thickness of the sample S can be obtained with high accuracy. Thus, it is possible to perform the abnormality detection of the sample S with high accuracy.

Moreover, even when the position of the sample S changes because of, for example, vertical swinging of the stage 2 or the like, the abnormality detection of the sample S can be performed with high accuracy.

Besides, for example, if the sample S is thick, tomographic information from the upper surface to the lower surface of the sample S cannot be obtained by OCT measurement from one direction, and accordingly the thickness of the sample S cannot be calculated. However, according to this embodiment, even in the case of the measurement of a thick sample, it is possible to obtain the thickness of the sample.

<Optical Property Measurement Method>

The optical property measurement apparatus according to the embodiments described above realizes the following optical property measurement method.

The optical property measurement method according to the embodiment includes a first detection step, an optical path length difference control step, a change amount information acquisition step, a second detection step, a tomographic information acquisition step, and a refractive index profile obtaining step.

The first detection step includes: splitting light output from a first light source into first signal light and first reference light; scanning a predetermined area of a sample with the first signal light; making the first signal light having passed through the sample interfere with the first reference light to generate first interference light; and detecting the first interference light generated.

The optical path length difference control step includes changing the optical path length difference between the optical path of the first signal light and the optical path of the first reference light based on the detection result of the first interference light obtained in the first detecting step.

The change amount information acquisition step includes acquiring change amount information indicating the amount of change in the optical path length difference due to the optical path length difference control step.

The second detection step includes: splitting light output from a second light source into second signal light and second reference light; scanning a predetermined area of the sample with the second signal light; making the second signal light having passed through the sample interfere with the second reference light to generate second interference light; and detecting the second interference light generated.

The tomographic information acquisition step includes acquiring tomographic information of the predetermined area of the sample based on the detection result of the second interference light obtained by the second detection step.

The refractive index profile obtaining step includes obtaining a refractive index profile in the predetermined area of the sample based on the change amount information acquired by the change amount information acquisition step and the tomographic information acquired by the tomographic information acquisition step.

According to the optical property measurement method, based on the results of both the optical property measurement and structure measurement of the sample, the abnormality detection of the sample can be performed with high accuracy.

Any of the processes described in the above embodiments may be performed through the optical property measurement method of the embodiment. For example, the optical property measurement method may include the following:

method of obtaining a refractive index profile in the refractive index profile obtaining step;
method of scanning a sample by the stage and the driver;
method of scanning a sample by the galvanometer scanner;
types of OCT applied to the second interference optical system and the tomographic information acquisition unit;
method of changing the optical path length of the reference optical path (second reference optical path) in OCT measurement;
processing method in the optical path length difference control step;
measurement method when the same light source is used as the first light source and the second light source; and
method of performing OCT measurement from both the upper and lower directions of the sample.

<Modification>

The embodiments described above are mere examples for embodying or carrying out the present invention, and therefore susceptible to several modifications and variations (omission, substitution, addition, etc.), all coming within the scope of the invention.

The various features of the above embodiments may be combined in an arbitrary way.

The optical path length difference controller 50, the change amount information acquisition unit 60, the tomographic information acquisition unit 70, and the operation controller 80 are realized by a processor(s) and a computer program(s), or a hardware circuit(s). In the former case, the computer program for realizing the above embodiments may be stored in an arbitrary recording medium that is readable by a computer. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like.

The program may be sent/received through a network such as the Internet or LAN.

What is claimed is:

1. An optical property measurement apparatus comprising:
    a first interference optical system configured to split an optical path of light output from a first light source into a first sample optical path and a first reference optical path, scan a predetermined area of a sample with first signal light that passes through the first sample optical path, make the first signal light that has passed through the first sample optical path interfere with first reference light that has passed through the first reference optical path to generate first interference light, and detect the first interference light generated;
    an optical path length difference controller configured to change an optical path length difference between the first sample optical path and the first reference optical path based on a detection result of the first interference light;
    a change amount information acquisition unit configured to acquire change amount information indicating an amount of change in the optical path length difference made by the optical path length difference controller;
    a second interference optical system configured to split an optical path of light output from a second light source into a second sample optical path and a second reference optical path, scan the predetermined area with second signal light that passes through the second sample optical path, make the second signal light that has passed through the second sample optical path interfere with second reference light that has passed through the second reference optical path to generate second interference light, and detect the second interference light generated;
    a tomographic information acquisition unit configured to acquire tomographic information of the predetermined area based on a detection result of the second interference light; and
    a refractive index profile obtaining unit configured to obtain a refractive index profile in the predetermined area based on the change amount information acquired by the change amount information acquisition unit and the tomographic information acquired by the tomographic information acquisition unit.

2. The optical property measurement apparatus according to claim 1, wherein, with respect to each measurement point in the predetermined area that is measured by performing scanning, the refractive index profile obtaining unit is configured to:
    calculate an optical distance in a thickness direction of the sample at the measurement point based on the change amount information;
    calculate a spatial distance in the thickness direction of the sample at the measurement point based on the tomographic information; and
    obtain refractive index of the sample at the measurement point by dividing the optical distance by the spatial distance.

3. The optical property measurement apparatus according to claim 1, further comprising
    a combining member configured to combine the first sample optical path and the second sample optical path; and
    an objective lens located between the combining member and the sample, wherein
    the first interference optical system is configured to irradiate the sample with the first signal light through the objective lens, and
    the second interference optical system is configured to irradiate the sample with the second signal light through the objective lens.

4. The optical property measurement apparatus according to claim 1, further comprising:
    a placement unit where the sample is placed; and
    a driver configured to move the placement unit in a direction substantially perpendicular to an optical axis of the first sample optical path and an optical axis of the second sample optical path to perform scanning.

5. The optical property measurement apparatus according to claim 1, further comprising a deflecting optical system located on the second sample optical path, and configured to deflect the second signal light directed toward the sample to perform scanning.

6. The optical property measurement apparatus according to claim 1, wherein
the second light source is a wavelength-swept light source, and
the tomographic information acquisition unit is configured to acquire the tomographic information based on the detection result of the second interference light obtained by the second interference optical system along with a sweep of wavelengths by the wavelength-swept light source.

7. The optical property measurement apparatus according to claim 1, wherein,
the second light source is a broad band light source,
the second interference optical system includes a spectrometer configured to detect spectra of the second interference light, and
the tomographic information acquisition unit is configured to acquire the tomographic information based on a detection result of the spectra obtained by the spectrometer.

8. The optical property measurement apparatus according to claim 1, wherein,
the second light source is a broad band light source,
the second interference optical system includes an optical path length modulator configured to modulate optical path length of the second reference optical path, and
the tomographic information acquisition unit is configured to acquire the tomographic information based on the detection result of the second interference light obtained by the second interference optical system along with the modulation of the optical path length.

9. The optical property measurement apparatus according to claim 1, wherein the second interference optical system includes an optical path length changing unit configured to change optical path length of the second reference optical path.

10. The optical property measurement apparatus according to claim 1, wherein
a single light source serves as the first light source and the second light source, and
the first interference optical system and the second interference optical system include a splitting optical system configured to split an optical path of light output from the single light source into the first sample optical path, the first reference optical path, the second sample optical path, and the second reference optical path.

11. The optical property measurement apparatus according to claim 1, further comprising a splitter configured to split an optical path of light output from the second light source into two optical paths, wherein
the second interference optical system is configured to split one of the optical paths obtained by the splitter into the second sample optical path and the second reference optical path,
the optical property measurement apparatus further comprising a third interference optical system configured to split another optical path obtained by the splitter into a third sample optical path and a third reference optical path, scan the predetermined area with third signal light that passes through the third sample optical path from an opposite direction to the second signal light, make the third signal light that has passed through the third sample optical path interfere with third reference light that has passed through the third reference optical path to generate third interference light, and detect the third interference light generated, wherein
the tomographic information acquisition unit is configured to acquire other tomographic information of the predetermined area based on a detection result of the third interference light, and
the refractive index profile obtaining unit is configured to obtain the refractive index profile based on the change amount information, the tomographic information, and the other tomographic information.

12. The optical property measurement apparatus according to claim 11, wherein
the refractive index profile obtaining unit includes a thickness distribution obtaining unit configured to obtain thickness distribution in the predetermined area based on the tomographic information and the other tomographic information acquired by the tomographic information acquisition unit, and
the refractive index profile obtaining unit is configured to obtain the refractive index profile based on the change amount information and the thickness distribution.

13. The optical property measurement apparatus according to claim 1, wherein the optical path length difference controller is configured to change the optical path length difference so that intensity of the first interference light detected by the first interference optical system becomes a predetermined value.

14. An optical property measurement method, comprising:
a first detection step including splitting light output from a first light source into first signal light and first reference light, scanning a predetermined area of a sample with the first signal light, making the first signal light having passed through the sample interfere with the first reference light to generate first interference light, and detecting the first interference light generated;
an optical path length difference control step of changing an optical path length difference between an optical path of the first signal light and an optical path of the first reference light based on a detection result of the first interference light;
a change amount information acquisition step of acquiring change amount information indicating an amount of change in the optical path length difference due to the optical path length difference control step;
a second detection step including splitting light output from a second light source into second signal light and second reference light, scanning the predetermined area with the second signal light, making the second signal light having passed through the sample interfere with the second reference light to generate second interference light, and detecting the second interference light generated;
a tomographic information acquisition step of acquiring tomographic information of the predetermined area based on a detection result of the second interference light; and
a refractive index profile obtaining step of obtaining a refractive index profile in the predetermined area based on the change amount information acquired by the change amount information acquisition step and the tomographic information acquired by the tomographic information acquisition step.

* * * * *